US00PP08645P

United States Patent [19]

Sturtz

[11] Patent Number: Plant 8,645

[45] Date of Patent: Mar. 15, 1994

[54] LOW MENTHOL MINT PLANT *MENTHA SPICATA* L. 'EROSPICATA'

[75] Inventor: George D. Sturtz, Albany, Oreg.

[73] Assignee: Aromatics, Inc., Salem, Oreg.

[21] Appl. No.: 968,031

[22] Filed: Oct. 27, 1992

[51] Int. Cl.[5] ..... A01H 5/00

[52] U.S. Cl. ..... Plt./100

[58] Field of Search ..... Plt. 100

[56] References Cited

U.S. PATENT DOCUMENTS 4,354,035 10/1982 Christ et al. ..... 560/75

5,017,397 5/1991 Nguyen et al. ..... 426/542

OTHER PUBLICATIONS

Guenther, "The Chemistry, Origin and Function of Essential Oils in Plant Life," The Essential Oils 1:17, 224–225, 390–392, 412–415 (1948).

Murray and Reitsema, "The Genetic Basis of the Ketones, Carvone, and Menthone in *Mentha crispa* L., " J. of American Pharmaceutic Association, Scientific Edition XLIII:612–613 Oct. 1954).

Murray, "The Genetic Basis for the Conversion of Menthone to Menthol in Japanese Mint," Genetics 46:925–929 (Jul. 1960).

Murray, "The Genetic Basis for a Third Ketone Group in *Mentha Spicata* L.," Genetics 46:931–937 (Jul. 1960).

Tucker et al., "The Origin of *Mentha* × *Gracilis* (Lamiaceae). II. Essential Oils," Economic Botany 45:200–215 (1991).

*Primary Examiner*—James R. Feyrer

*Assistant Examiner*—Erich E. Veitenheimer

*Attorney, Agent, or Firm*—Klarquist Sparkman Campbell Leigh & Whinston

[57] ABSTRACT

A novel *Mentha spicata* mint plant characterized by its resistance to verticillium wilt and mint rust, and an essential oil with a relatively low l-menthol content and high menthone content. The oil, which has at most only minor amounts of piperitone and l-carvone, is characterized by peppermint-like taste and a hot odor.

2 Drawing Sheets

1

The present invention relates to a new and distinct variety of mint plant of the species botanically known as *Mentha spicata.* I have named by new variety "Erospicata."

I discovered my new variety as a chance seedling from a self pollination of a parent plant *M. spicata* L. var *crispata* Schrad. The seedling was grown in a cultivated area of my nursery in Oregon. My attention was first directed to the new plant because of its hot smell. I further observed disease resistance of this plant to verticillium wilt and mint rust. Analysis of the oil of this plant showed that it was quite unusual and distinct from other *M. spicata.*

Close observations of the new seedling and continued observations of progeny thereof subsequently asexually propagated under my direction on land near Corvallis, Oreg., by rooting cuttings, has confirmed that the unique characteristics of my new variety are a result of a seedling variation. I am therefore convinced that my new mint plant represents a new and improved variety of *Mentha spicata,* as particularly evidenced by the following unique combination of characteristics, which have proven firmly fixed, or outstanding, and which distinguish it from all other varieties of this species.

1. Low l-menthol content and high menthone content as compared to the oil of its *Mentha spicata* parent.

2. Only minor amounts of piperitone and l-carvone in the oil produced by the plant.

3. Disease resistance to verticillium wilt and mint rust.

4. A hot odor as opposed to the cool odor of its parent.

The accompanying photographs depict the color of my new variety of mint plant as nearly true as is reasonably possible to make the same in a color illustration of this character.

2

Figure 2:
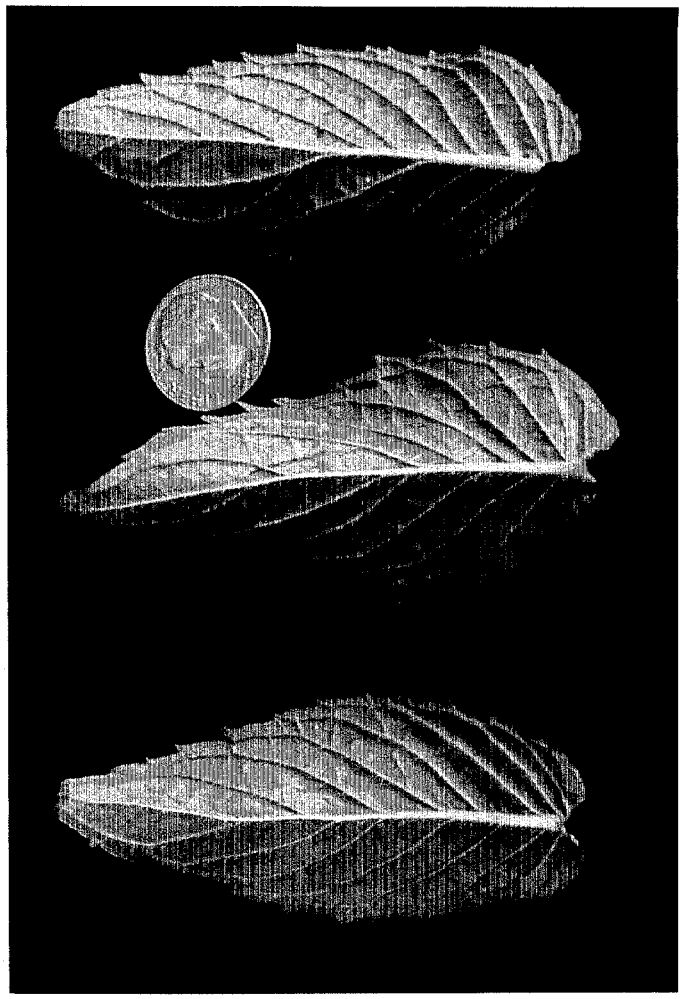
FIG. 2 is an enlarged photograph showing a leaf of the plant of FIG. 1.
Figure 1:
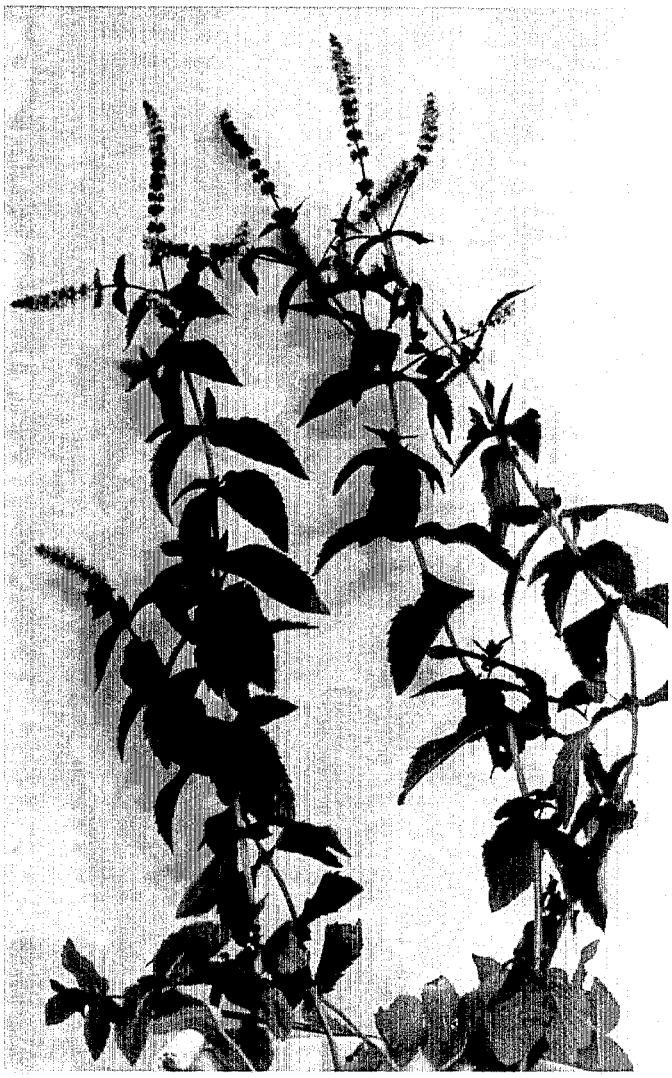
FIG. 1 is a color photograph of a plant of the present invention.

One of the primary distinguishing features of my new mint plant over other mint plants of this species is that it has a characteristic peppermint taste and smell, yet its oil contains much lower levels of menthol and much higher levels of menthone. The *M. spicata* plant of the present invention produces an essential oil with an l-menthol content of less than about 5% by weight, a piperitone content of less than about 2%, and has more than about 50% l-menthone, and is substantially free of l-carvone. The essential oil, preferably comprises less than about 1% by weight l-menthol, less than about 1% piperitone, and at least 50% l-menthone. In particularly preferred embodiments, the essential oil comprises 55–60% l-methone, less than about 1% l-menthol, less than about 1% piperitone, and is substantially free of l-carvone, menthofuran, menthyl acetate, and trans-sabinene hydrate. The oil contains sufficient amounts of menthone that it has the organoleptic properties of peppermint oil.

The low menthol content of the essential oil is important because menthol is an alcohol that irritates nasal, oral and gastrointestinal epithelium. Hence only very small amounts of conventional peppermint oil can be added to ingestible products such as candy. The plant of the present invention has retained sufficient menthone content to provide a "hot" peppermint taste and odor, but menthol is substantially absent from the oil. The absence of this alcohol helps avoid nasal and gastrointestinal irritation, while the menthone provides peppermint-like organoleptic properties. My new mint plant also expresses an oil that is low in carvone and piperitone content. The substantial absence of carvone and piperitone is important because these substances provide a taste that is organoleptically undesirable in peppermint oil. Carvone provides a spearment taste, while piperitone imparts a bitter taste.

The mint plant of the present invention has an essential oil that, when analyzed by gas chromatographic analysis, includes the following weight percentages of menthone, carvone, menthol and piperitone:

| | |
|---|---|
| l-menthone | >40 |
| d-isomenthone | >15 |
| carvone | <.01 |
| l-menthol | <1 |
| piperitone | <1 |

An example of the plant of the present invention is deposited with the U.S.D.A. National Clonal Germplasm Repository in Corvallis, Oreg., under accession number MEN625.

Strain 86-183

The Erospicata variety is referred to herein as strain 86-183. Strain 86-183 relates to a new variety of mint plant originating as an $S_1$ selection from the self-pollination of a clonal strain of *M. spicata* L. The parent plant of strain 86-183 is a wild spearment obtained from the National Germplasm Repository in Corvallis, Oreg., under accession no. MEN57. This parent strain was originally numbered 71-62 by the originator, Dr. J. M. Murray, of the A. M. Todd Co. in Kalamazoo, Mich. Clone 71-62 was called *M. crispa* L. or *M. spicata* L. var *crispata* Schrad. It is a fertile allotetraploid plant with a chromosome number of 48. The 71-62 plant is resistant to verticillium wilt (*Verticillium albo-atrum*) and is believed to be immune to mint rust (*Puccinia menthae*). The 71-62 strain is glabrous and yields an essential oil containing about 70% of the ketone carvone, and less than 1% menthol, but it also has less than 1% menthone. It therefore lacks the odor or taste of peppermint that would be provided by menthol or menthone, yet has the spearmint odor and taste provided by carvone. The leaves are crisped or ruffled, hence the original name crispa. It has been shown that carvone-odored *M. crispa* has a genotype that segregates 16 spearmint in a 12 high carvone: 3 high menthone: 1 high piperitone ratio in the $S_1$ progeny. A major consideration in the use of the wild spearmint parent, *M. crispa* (71-62), was its excellent resistance to verticillium wilt and leaf rust.

General Objectives of this Breeding Program

The broad objectives of this breeding program were to try bring together in one plant the characteristics deemed necessary for a successful commercial essential oil crop. The two most important traits were disease resistance to wilt and rust, and an essential oil high in the major peppermint flavor components and low in undesirable compounds. High vigor and aggressive stolon development were also considered desirable traits. The parent plant (71-62) met the criteria of disease resistance and vigor.

Breeding Program History

The parent plant (71-62) was self pollinated in the summer, and seeds from that plant were sown in a greenhouse in the following spring. Approximately 400 seedlings were selected and grown in 1 $m^2$ plots for three years. The plots were watered, weeded and fertilized alike and mowed at flowering to maintain clonal purity. Plots were initially screened for menthone types by organoleptic methods, primarily by detecting a characteristic menthone odor. Approximately 70 plots had at least some menthone odor, but most were discarded for undesirable traits such as disease susceptibility or a "cool" menthol sensation upon organoleptic sampling. Plot number 86-183 was selected as a superior plant due to its vigorous growth habits and odor quality, having a sweet and hot odor. Subsequent chromatographic analysis of the essential oil revealed that the oil contained at least approximately 70% of the ketone menthone, which includes its isomers such as l-menthone and d-isomenthone. No disease was evident in the three years of tests with this strain.

This strain (86-183) was vegetatively propagated and grown in a 3 $m^2$ plot in two subsequent years to study oil yield, quality and disease resistance. Then it was grown on several 0.5 hectare plots by farmers in Oregon's Willamette Valley and Madras, Oreg., to study the effects of site and harvest times on oil yield and quality.

A Taxonomic Description of Strain 86-183

Strain 86-183 is a herbaceous perennial, becoming woody at the base of the stems late in the growing season. It has upright stems from the tips of horizontal rhizomes which spread vigorously in a lateral direction during the fall, winter, and early spring. Field grown plants may attain a height of 1 meter, but more commonly 6–8 dm. Herbage is glaborous except for some hairs on the veins on the lower surface of the leaves and the calyx teeth. Leaves are sessile, lanceolate, serrate (8–10 teeth on each side), and occasionally crisped. The largest cauline leaves are up to 7 cm long and 2.5 cm wide. Stems are branched in the upper portions with terminal, slender, leafless spikes of many (12–15) whorls of small flowers. Flower clusters (whorls) are subtended by a pair of lanceolate to linear bracts, the lower whorls being somewhat remote. Mature (containing mature nutlets) calyces are approximately 2.0 mm long, the upper portion dissected into 5 teeth that are less than 1 mm long with marginal and terminal trichomes (hairs). Five petals are fused into a two-lipped corolla that is pale lavender with darker splotches. The stigma is two-lobed and exserted. Fruits are small (less than 1 mm) dark brown nutlets, four per calyx. The chromosome number is $2n=48$.

The R.H.S. (Royal Horticultural Society) color of the top of the leaf is Green group 139A, while the bottom of the leaf is Green group 137C. The lavender flowers are Purple group 76C.

Strain 86-183 was very resistant to verticillium wilt and leaf rust when planted in wilt infected fields of the Willamette Valley. Only 0–3 plants in a field of 2000 plants were observed to develop these diseases in one trial. This resistance was apparently inherited from the parent (71–62) which is also highly resistant to these diseases. To demonstrate the disease resistance of strain 86-183, field trials were planted Apr. 3, 1992, in Talbot, Oreg. Two thousand plants of strain 86-183 were evaluated for mint rust (*Puccinia menthae*) and verticillium wilt (*Verticillium albo-atrum*). No incidence of rust or verticillium wilt were noted between Jun. 1, 1992, and Oct. 1, 1992.

Strain 86-183 has very aggressive stolons, growing under the soil surface, thereby providing the plant with protection from adverse weather conditions and mechanical damage.

Essential oils were obtained from the parent plant (71-62) and the strain of the present invention (86-183). The essential oil yield of strain 86-183 varies with climatic, cultural and other environmental factors. Willamette Valley trials in 1992 produced oil yields of at least 112 kg/hectare. Essential oils were obtained by steam distillation of the volatile oil of the plants using a method described in the publication *Mint Farming*, Agricultural Research Service, USDA (1963). the essential oil was then analyzed by GC/MS/DS using a Finnigan 1015C MS (mass spectrometer) interfaced by a glass-jet helium separator to a Varian 1400 GC (gas chromatograph). The glass GC column was obtained from Supelco Inc.; it was 0.75 mm ID and 60 M in length. The liquid phase was a 1 micron chemically bonded layer of Supelcowax 10 (functionally equivalent to Carbowax 20M). Samples were injected neat (without splitting). The GC injector was 220° C. and the GC column was held at 80° C. for 5 minutes, and then programmed to increase at 2° C./min to 190° C. Since some components co-eluted on the Supelcowax 10 column, the oil was also run on a non-polar (Supelco SPB-1; methyl silicone) glass column of exactly the same dimensions, and using the same temperature program as before, but the injection temperature was now 230° C.

Data was acquired and processed using a Riber 400 data system. Off-line file searching using an IBM-AT made use of a database file named KOVATS that was created under the PARADOX program from Borland International. The KOVATS database contains Kovats indices for two GC liquid phases, as well as the MW and the six most abundant ions in the mass spectrum.

Some of the components identified in the essential oil are listed in Table 1:

TABLE 1

Weight percent composition of the essential oils of *Menta spicata* L. strains 71-62 and 86-183

| Constituent | Parent (71-62) | Strain (86-183) |
|---|---|---|
| *l-menthone | 0.94 | 58.80 |
| *d-isomenthone | 0.05 | 17.30 |
| *l-carvone | 71.60 | <0.01 |
| *beta caryophyllene | 4.27 | 0.04 |
| l-menthol | 0.32 | 0.05 |
| *germacrene D | 0.03 | 5.41 |
| piperitone | <0.01 | 0.20 |

*notable differences in the composition of the oils form strains 71-62 and 86-183.

These results show that 86-183 differs from 71-62 in several important respects. Strain 86-183 is higher in essential oil content of l-menthone and d-isomenthone. Most notably, strain 86-183 has a much higher l-menthone content (58.8% vs. 0.94%), d-isomenthone content (17.30 vs. 0.05%), a lower l-menthol content (0.05% vs. 0.32%), and is substantially free of carvone as compared to the 71.6% carvone content of strain 71-62. The total menthone content (d-isomenthone and l-menthone) of strain 86-183 is greater than 75% (i.e., 76.1%). Strain 86-183 also has less than about 6% germacrene D, compared to less than 1% in strain 71-62.

Gas chromatographic analysis was also performed on a second sample from another plant of strain 86-183, and the results are shown in Table 2 below.

TABLE 2

Gas Chromatographic Analysis of Essential Oil From a Sample of Strain 86-183, by Weight Percent

| | |
|---|---|
| l-menthone | 56.32 |
| d-isomenthone | 16.64 |
| l-carvone | <0.01 |

TABLE 2-continued

Gas Chromatographic Analysis of Essential Oil From a Sample of Strain 86-183, by Weight Percent

| | |
|---|---|
| l-menthol | 0.17 |
| germacrene D | 6.47 |
| piperitione | 1.15 |

For comparison, gas chromatographic analysis was performed on spearmint oil obtained from a *Mentha spicata crispa* Scotch plant, in this case some Farwest Scotch Spearmint Oil, 1991 crop, obtained from Aromatics, Inc., of Salem, Oreg.

TABLE 3

Gas Chromatographic Analysis, by Weight Percent of Selected Components of Spearmint Oil as Comparison

| | |
|---|---|
| l-menthone | 0.77 |
| d-isomenthone | 0.13 |
| l-menthol | 0.01 |
| l-carvone | 64.93 |

The essential oil of this spearmint plant was essentially free of menthol and menthone (less than 1% of each), but was high in l-carvone concentration (more than about 60%) which gave the oil the organoleptic properties of spearmint.

As a further comparison, a gas chromatographic analysis was performed on peppermint oil obtained from a conventional *Mentha piperate* plant Murray Mitchum, in this case peppermint oil from Aromatics, Inc., of Salem, Oreg.

TABLE 4

Gas Chromatographic Analysis, by Weight Percent, of Selected Components of Peppermint Oil as Comparison

| | |
|---|---|
| l-menthone | 22.24 |
| d-isomenthone | 3.01 |
| l-menthol | 42.48 |
| piperitone | 0.58 |

This peppermint oil contains characteristically high concentrations of l-menthol and l-menthone. It includes more than 40% 1-menthol and more than 20% l-menthone. This level of menthone provides a characteristic peppermint taste, but the presence of l-menthol in more than trace amounts (e.g., more than 1% or 2%) provides a "cool" organoleptic sensation and produces mucosal irritation.

To demonstrate the consistently high level of carvone in spearmint oil (*Mentha spicata* native), a gas chromatographic analysis was also performed on Farwest Native Spearmint Oil from Aromatics, Inc., of Salem, Oreg.

TABLE 5

Gas Chromatographic Analysis, by Weight Percent, of Selected Components of Farwest Native Spearmint Oil
* Concentration = Relative Area % *

| | |
|---|---|
| l-menthone | 0.03 |
| d-isomenthone | 0.05 |
| l-menthol | 0.18 |
| l-carvone | 59.48 |

This spearmint oil contains characteristically low concentrations (less than 1%) of menthone and menthol, but is very high in carvone content. The oil has more than 50% l-carvone, which gives it a strong characteristic spearmint taste.

Distinguishing Characteristics of Strain 86-183

Some of the distinguishing characteristics of the essential oil of strain 86-183 are shown in the following Table 6, which compares that oil to peppermint oil and spearmint oil, and Clone 199 that was described by Tucker in *Economic Botany* 45(2):200–215 (1991).

TABLE 6

Comparison of Peppermint Oil, Spearmint Oil and Essential Oil of Strains 86–183 and Spic-199

| Oil Compounds | 86–183 | Peppermint | Spearmint | Spic-199 |
|---|---|---|---|---|
| l-menthol | 1% Max | 35–45% | 0% | 0% |
| l-carvone | 1% Max | 0% | 50%–70% | 0% |
| menthyl acetate | 1% Max | 3–5% | .01–.10% | .13% |
| l-menthone | 50–60% | 18–20% | .03–1.0% | 51.73% |
| piperitone | 2% Max | .10–1% | 0% | 10.65% |

Some of the morphological characteristics that distinguish strain 86-183 from Spic 199 are set forth in Table 7:

TABLE 7

A Morphological Comparison of Spic 199 and Strain 86–183

| | Spic-199 | Strain 86–183 |
|---|---|---|
| Leaf blade | flat | may be crisped |
| Leaf shape | lanceolate | lanceolate |
| Leaf attachment | petiole 0.5 cm long | sessile (no petiole) |
| Leaf margin | serrate | serrate |
| Leaf length | longest 5 cm | longest 7 cm |
| Leaf width | <2 cm | 2.5 cm (greater than 2 cm) |
| Hairness | occasional hair on veins otherwise glaborous | veins hairy, otherwise glaborous |
| Plant color | dark green with purple stems and veins | light green, no other coloration |
| Plant height | <5 dm | 6–8 dm to 1 meter |
| Chemotype | menthone, 10% piperitone | menthone, <1% piperiton |

I claim:

1. A new and distinct variety of a disease-resistant mint plant, substantially as shown and described, characterized particularly as to novelty by its production of an oil with a relatively low l-menthol content and high menthone content, when compared to the oil of its *Mentha spicata* parent, and at most only minor amounts of piperitone and l-carvone, said oil having a peppermint-like taste and a hot odor.

* * * * *